(12) United States Patent
Uemura

(10) Patent No.: US 8,126,673 B2
(45) Date of Patent: Feb. 28, 2012

(54) HIGH RATE LINE-BY-LINE CALCULATION METHOD AND PROGRAM BY FORKED LINE TYPE RESOLUTION

(75) Inventor: Nobuyuki Uemura, Tokyo (JP)

(73) Assignee: Fujitsu FIP Corporation, Tokyo (JP)

( * ) Notice: Subject to any disclaimer, the term of this patent is extended or adjusted under 35 U.S.C. 154(b) by 1453 days.

(21) Appl. No.: 10/573,869

(22) PCT Filed: Aug. 26, 2004

(86) PCT No.: PCT/JP2004/012301
§ 371 (c)(1),
(2), (4) Date: Jan. 5, 2007

(87) PCT Pub. No.: WO2005/033640
PCT Pub. Date: Apr. 14, 2005

(65) Prior Publication Data
US 2007/0097122 A1  May 3, 2007

(30) Foreign Application Priority Data
Sep. 30, 2003 (JP) .................................. 2003-342605

(51) Int. Cl.
G06F 19/00 (2011.01)
G01J 3/00 (2006.01)
(52) U.S. Cl. ...................................... 702/115; 423/308
(58) Field of Classification Search .................. 702/115; 423/308
See application file for complete search history.

(56) References Cited

U.S. PATENT DOCUMENTS 5,838,008 A  11/1998  Esler et al.
7,385,803 B2 *  6/2008  Alberti et al. ................. 361/524

FOREIGN PATENT DOCUMENTS

JP  2001-506753 A  5/2001

OTHER PUBLICATIONS

European Search Report dated Nov. 23, 2009.
Uchiyama et al; "Line-by-Line computation of the atmospheric absorption spectrum using the decomposed Voigt line shape" Journal of Quantitative Spectroscopy and Radiative Transfer, vol. 47, No. 6, Jun. 1, 1992 pp. 521-532.

(Continued)

Primary Examiner — Bryan Bui
(74) Attorney, Agent, or Firm — Pearne & Gordon LLP

(57) ABSTRACT

The invention offers a calculation method and program capable of performing line-by-line calculations using a Voigt function at speeds of 50-100 times what is conventional. The Voigt function is divided into a first range around the peak and a skirt portion not contained in the first range. The first range is replaced by a cubic function, and the skirt portion is taken as the Voigt function to perform calculations in predetermined ranges of equal intervals. Furthermore, the peak area of the first range is replaced by a cubic function, and the skirt portion is taken as a function representing the difference between the Voigt function and the cubic function to perform calculations in second predetermined intervals smaller than the aforementioned first predetermined intervals. This is repeated until the desired level of precision is reached. Additionally, interpolation is performed by dividing these predetermined intervals into four or five parts.

15 Claims, 3 Drawing Sheets

OTHER PUBLICATIONS

Lynas-Gray et al; "Voigtl—a fast subroutine for Voigt function evaluation on vector processors", Computer Physics Communication, vol. 75, No. 1-2, Apr. 1, 1993, pp. 135-136, (only two pages in record).

Apt J et al; "Comparison of band model an dintegrated line-by-line synthetic spectra for methane in the 2.3 mum region" Journal of Quantitative Spectroscopy and Radiative Transfer, vol. 26, No. 5, Nov. 1, 1981 pp. 431-442.

De Mul, F.F.M., et al. The MCGA (Multiple Cubic Gradient Approximation) Method for the Analysis of Raman Spectra. IN: Journal of Raman Spectroscopy, vol. 21; 1990; pp. 725-736.

Uemura, N; Fujitsu FIP Corporation, Tokyo, JP. Windows-based line-by-line radiative transfer computation using Mathcad. (online) ASSFTS 11 workshop, Oct. 2003. retrieved from the internet URL:http://www-imk.fzk.de/asf/ame/assfts/P_I_B_Uemura_N.pdf. 11 pages.

Lynas-Gray, A.E. Voigtl—a fast subroutine for Voigt function evaluation on vector processors. IN: Computer Physics Communications, vol. 75; 1993; pp. 135-142.

English translation of International Search Report of International application No. PCT/JP2004/012301.

* cited by examiner

HIGH RATE LINE-BY-LINE CALCULATION METHOD AND PROGRAM BY FORKED LINE TYPE RESOLUTION

TECHNICAL FIELD

The present invention relates to high-speed line-by-line calculation of the absorption coefficient spectra of gas molecules necessary for atmospheric observations.

BACKGROUND ART

While the Earth's atmosphere receives electromagnetic radiation from the sun, it is itself releasing electromagnetic radiation mainly in the infrared region into space. This electromagnetic radiation interacts such as by absorption, radiation and scattering with gas molecules, clouds, aerosols and the like present in the atmosphere. By measuring changes in the spectral distribution of electromagnetic radiation caused by such interactions with the atmosphere (theoretical calculations of such distributions are referred to as radiative transfer calculations) using sensors on land or in airplanes or satellites, it is possible to study the air temperature, air pressure and concentrations of atmospheric trace gas constituents.

While a technique known as line-by-line calculation is used for radiative transfer calculations of the atmosphere, line-by-line calculations involve a enormous number of calculations. For this reason, the calculation time becomes extremely long, making it practically difficult to perform calculations over a wide spectral range at high speeds using personal computers or the like. Additionally, there are methods that make use of data obtained in line-by-line calculations beforehand involving table lookup routines as methods for avoiding the problem discussed above, but such methods have the drawback of requiring large data files. Additionally, other algorithms not requiring prior calculation have fared no better than about 20 times the speed of line-by-line calculations.
Non-Patent Publication 1: Akihiro Uchiyama, "Line-by-Line Computation of the Atmospheric Absorption Spectrum Using the Decomposed VOIGT Line Shape", *J. Quant. Spectrosc. Radiat. Transfer*, Vol. 47, No. 6, pp. 521-532, 1992.

DISCLOSURE OF THE INVENTION

Problems to be Solved by the Invention

Due to the problems mentioned above, calculation methods capable of line-by-line calculations at high speed have been sought, and the present invention offers such a calculation method and program.

Means for Solving the Problems

The present invention relations to a Voigt function approximation calculating program used for line-by-line calculations, said program performing:

(1) a step of dividing a domain of a Voigt function into a first range around the peak of the Voigt function and a skirt portion not contained in the first range, replacing the first range with a cubic function, calculating the values and derivatives of said cubic function and the Voigt function in the skirt portion for each of first predetermined intervals, and connecting said cubic function and said Voigt function at points of connection thereof using the values and derivatives of both functions;

(2) a step of adding together the results of step (1) for a plurality of absorption lines;

(3) a step of calculating the function values and derivatives for the results of step (2) by interpolation over intervals smaller than said first predetermined intervals;

(4) a step of dividing said first range into a second range near the peak and a skirt portion not contained in the second range, replacing said second range of a "function representing the difference between the Voigt function and said cubic function" with a cubic function, and calculating values and derivatives of said cubic function and said "function representing the difference between the Voigt function and said cubic function" in the skirt portion for each of second predetermined intervals;

(5) a step of connecting said cubic function and said "function representing the difference between the Voigt function and said cubic function" at points of connection thereof using the values and derivatives of both functions;

(6) a step of adding the results of steps (4) and (5) to the results of step (3) for a plurality of absorption lines;

(7) a step of calculating the function values and derivatives for the results of step (6) by interpolation over intervals smaller than said second predetermined intervals; and (8) a step of adding the values of the "function representing the difference between the Voigt function and said cubic function" to the results of step (7) for a plurality of absorption lines in said second range.

A method using the above steps allows a Voigt function to be calculated at high speed using a cubic function.

In addition thereto, the steps (5) through (8) may be repeated one or more times until a third predetermined interval is reached. As a result, it is possible to obtain detailed results with small calculation intervals. The first through third predetermined intervals can be determined as described below.

The first predetermined interval for the widest sub-function is $j^{kmax}dv$. Here, j is a single-digit natural number, dv is the increment in wave number, and kmax is the largest natural number satisfying the relationship $j^{kmax+2}pdv \leq Vmax$. However, Vmax represents the maximum calculation range from the center of the absorption line, and p is a natural number (p=1, 2, 3) for controlling the calculation precision.

The most specific third predetermined interval is $j^{kmin}dv$. Here, j is a single-digit natural number of about 2-6, dv is the increment of the wave number, and kmin is the maximum non-negative decimal fraction (0 when non-existent) satisfying the relationship $j^{kmin}pdv \leq \alpha$ (a being approximately $\gamma/4$). However, $\gamma$ is an approximate value of the full-width at half-max of the absorption line, and p is a natural number (p=1, 2, 3) for controlling the calculation precision.

A method in accordance with any one of claims 1-4, wherein the second predetermined intervals are determined using the following equation.

For the sub-function with the (k−kmin+1)-th smallest width, the predetermined interval is $j^k dv$. Here, j is a single-digit natural number, dv is the increase in wave number and k is such that $kmin \leq k < kmax$.

For a quartered interpolation, the interpolation is calculated with j set to 4, using the function values $y_0$, $y_1$ and function derivative values $y_0'$, $y_1'$ at $x_0$, $X_1$ in the interpolation interval $(x_0, x_1)$, with the below-given Equation (1) as a function value interpolation equation, Equation (2) as a function derivative value interpolation equation and $\epsilon$ as a non-negative decimal fraction.

[Eq. 1]

$$\begin{pmatrix} y_a \\ y_b \\ y_c \end{pmatrix} = \frac{1}{64}\begin{pmatrix} 54-6\varepsilon & 10+6\varepsilon & 9(1-\varepsilon) & -3(1-\varepsilon) \\ 32 & 32 & 8(1-\varepsilon) & -8(1-\varepsilon) \\ 10+6\varepsilon & 54-6\varepsilon & 3(1-\varepsilon) & -9(1-\varepsilon) \end{pmatrix}\begin{pmatrix} y_0 \\ y_1 \\ (x_1-x_0)y_0' \\ (x_1-x_0)y_1' \end{pmatrix} \quad (1)$$

[Eq. 2]

$$\begin{pmatrix} y_a' \\ y_b' \\ y_c' \end{pmatrix} = \frac{1}{16(x_1-x_0)} \quad (2)$$

$$\begin{pmatrix} -18+2\varepsilon & 18-2\varepsilon & 3(1-\varepsilon) & -5(1-\varepsilon) \\ -24+8\varepsilon & 24-8\varepsilon & -4(1-\varepsilon) & -4(1-\varepsilon) \\ -18+2\varepsilon & 18-2\varepsilon & -5(1-\varepsilon) & 3(1-\varepsilon) \end{pmatrix}\begin{pmatrix} y_0 \\ y_1 \\ (x_1-x_0)y_0' \\ (x_1-x_0)y_1' \end{pmatrix}$$

For an interpolation divided into five parts, the interpolation is calculated with j set to 5, using the function values $y_0$, $y_1$ and function derivative values $y_0'$, $y_1'$ at $x_0$, $x_1$ in the interpolation interval $(x_0, x_1)$, with the below-given Equation (3) as a function value interpolation equation, Equation (4) as a function derivative value interpolation equation and E as a non-negative decimal fraction.

[Eq. 3]

$$\begin{pmatrix} y_a \\ y_b \\ y_c \\ y_d \end{pmatrix} = \quad (3)$$

$$\frac{1}{125}\begin{pmatrix} 112-12\varepsilon & 13+12\varepsilon & 16(1-\varepsilon) & -4(1-\varepsilon) \\ 81-6\varepsilon & 44+6\varepsilon & 18(1-\varepsilon) & -12(1-\varepsilon) \\ 44+6\varepsilon & 81-6\varepsilon & 12(1-\varepsilon) & -18(1-\varepsilon) \\ 13+12\varepsilon & 112-12\varepsilon & 4(1-\varepsilon) & -16(1-\varepsilon) \end{pmatrix}\begin{pmatrix} y_0 \\ y_1 \\ (x_1-x_0)y_0' \\ (x_1-x_0)y_1' \end{pmatrix}$$

[Eq. 4]

$$\begin{pmatrix} y_a' \\ y_b' \\ y_c' \\ y_d' \end{pmatrix} = \frac{1}{25(x_1-x_0)} \quad (4)$$

$$\begin{pmatrix} -24-\varepsilon & 24+\varepsilon & 8(1-\varepsilon) & -7(1-\varepsilon) \\ -36+11\varepsilon & 36-11\varepsilon & -3(1-\varepsilon) & -8(1-\varepsilon) \\ -36+11\varepsilon & 36-11\varepsilon & -8(1-\varepsilon) & -3(1-\varepsilon) \\ -24-\varepsilon & 24+\varepsilon & -7(1-\varepsilon) & 8(1-\varepsilon) \end{pmatrix}\begin{pmatrix} y_0 \\ y_1 \\ (x_1-x_0)y_0' \\ (x_1-x_0)y_1' \end{pmatrix}$$

Additionally, the invention offers a method for achieving high speeds, when assuming the Voigt function to be $K(x, y)$ and the difference from the Voigt profile of the absorption line to be $K(x, y)+f(x)$, by replacing $$\tilde{K}(x, y) = AK(x, y) + Bf(x) \quad [\text{Eq. 5}]$$

and $$\frac{\partial K(x, y)}{\partial x} \quad [\text{Eq. 6}]$$

Furthermore, the invention offers a method for achieving high speeds, when assuming the difference from the Voigt profile to be $K(x, y)f(x)$, by replacing $$\tilde{K}(x, y) = K(x, y)f(x) \quad [\text{Eq. 7}]$$

and $$\frac{\partial \tilde{K}(x, y)}{\partial x} = \frac{\partial K(x, y)}{\partial x}f(x) + K(x, y)\frac{\partial f(x)}{\partial x} \quad [\text{Eq. 8}]$$

Additionally, in line-mixing correction:

$$\tilde{K}(x, y) = AK(x, y) + BL(x, y) \quad [\text{Eq. 9}]$$

and $$\frac{\partial \tilde{K}(x, y)}{\partial x} = -2\left[(Ax+By)K(x, y) - (Ay-Bx)L(x, y) - \frac{B}{\sqrt{\pi}}\right] \quad [\text{Eq. 10}]$$

Here, $L(x, y)$ is the imaginary component of the function $w(z)$ (the real part is the Voigt function), where complex number $z=x+iy$, defined by the following equation.

$$w(z) = \quad [\text{Eq. 11}]$$

$$\frac{i}{\pi}\int_{-\infty}^{\infty}\frac{\exp(-t^2)}{z-t}dt = \exp(-z^2)\text{erfc}(-iz) = K(x, y) + iL(x, y)$$

($\text{erfc}(z)$ is a complex complementary error function).

Furthermore, the invention offers a device for performing the method of the present invention by loading the method described above as a program.

EXPLANATION OF REFERENCE NUMBERS

1 Voigt function
2 first range
3 skirt portion
4 function contained in first range
5 portion not contained in first range

BEST MODE FOR CARRYING OUT THE INVENTION

Figure 1:
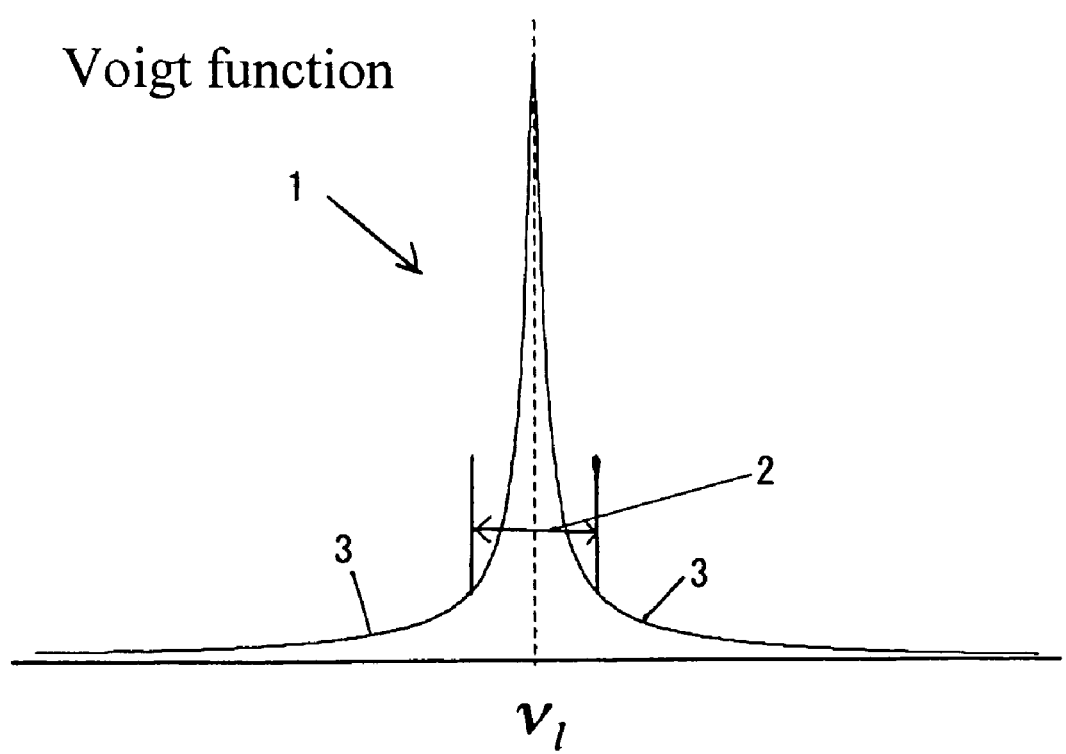
FIG. 1 is a schematic view of a Voigt function.

An embodiment of the present invention shall be described below. FIG. 1 is a diagram showing the shape of a Voigt function 1. According to the present invention, this Voigt function 1 is first divided into sub-functions. These sub-functions are in a first range 2 around the peak and a skirt portion 3 outside the first range 2. This first range 1 is replaced by a cubic function, and the portion not contained in the first range, in other words, the skirt portion, is calculated with the Voigt function.

Figure 2:
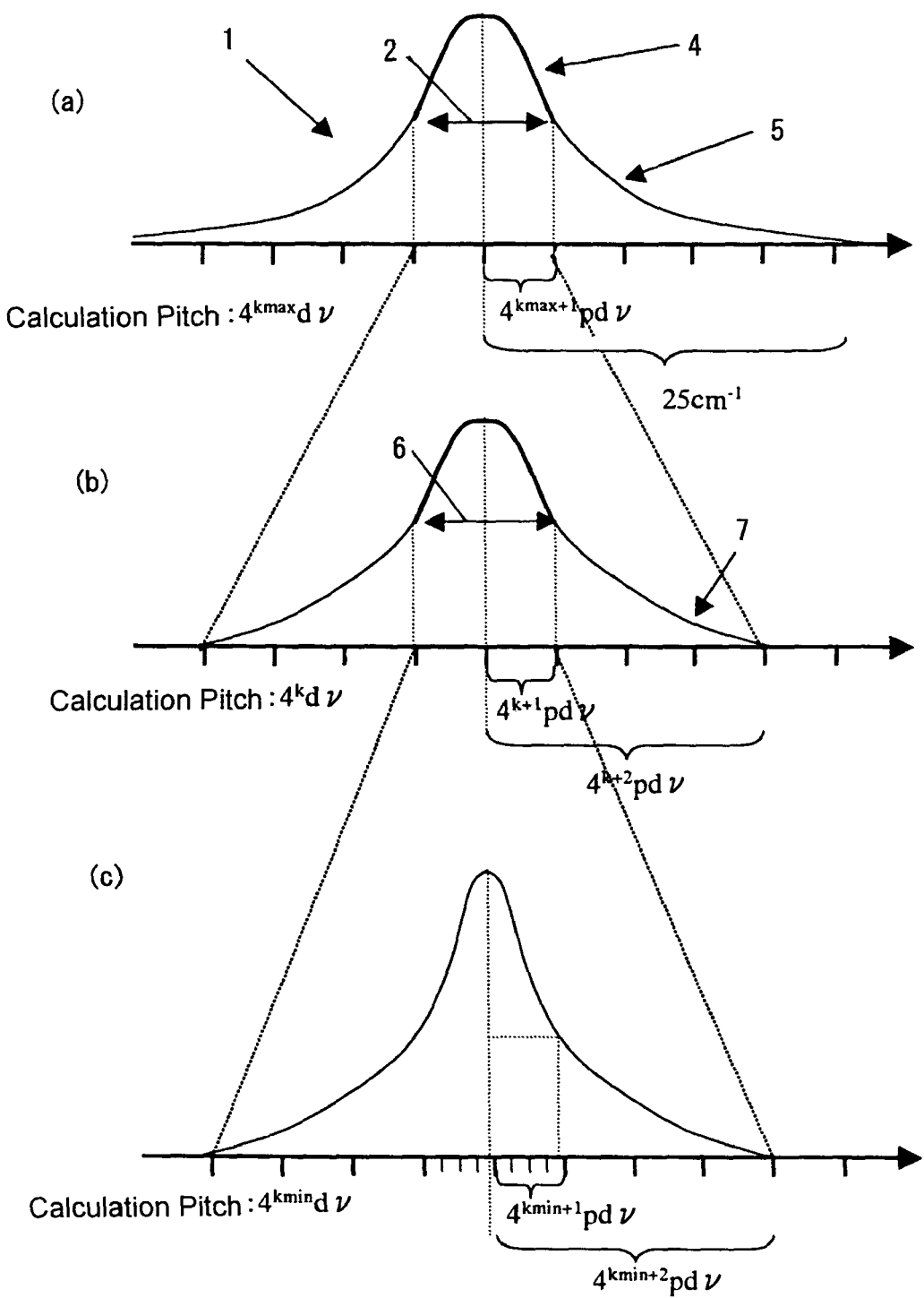
FIG. 2 is a diagram showing how a Voigt function is divided into sub-functions according to the method of the present invention.

The details of the calculation method are shown in FIG. 2. As shown in FIG. 2(*a*), the function 4, which is the portion of the Voigt function 1 contained in the first range 2, is replaced by a cubic function. At this time, the cubic function is determined so as to smooth the connections by matching the derivatives of the functions at the points of connection between the cubic function and the Voigt function. Additionally, the portion 5 not contained in the first range is calculated by the Voigt function. The calculation is performed over a first predetermined interval, indicated by $j^{kmax}dv$ where dv is the change in wave number. Here, j is a single-digit natural number, and kmax is the largest natural number satisfying the relationship $j^{kmax+2}pdv \leq Vmax$. Vmax may, for example, be 25 cm$^{-1}$. Additionally, j is normally a number of about 2-6, and is preferably 4. Also, Vmax represents the calculation range from the center of the absorption line, and p is a natural number for controlling the calculation precision, p preferably having a value of 1, 2 or 3.

Results calculated in this way are added together for a plurality of absorption lines. At this stage, the result is an approximate value calculated in the first predetermined interval.

Next, unevaluated points are calculated over an interval smaller than the first predetermined interval. That is, the unevaluated points are interpolated over intervals obtained by quartering the first predetermined interval. The calculation of the point of division is performed by the following interpolation formula.

The function values $y_0$, $y_1$ and function derivative values $y_0'$, $y_1'$ at $x_0$, $x_1$ in the interpolation interval $(x_0, x_1)$ can be determined by the following two equations:

[Eq. 12]

$$\begin{pmatrix} y_a \\ y_b \\ y_c \end{pmatrix} = \frac{1}{64} \begin{pmatrix} 54-6\varepsilon & 10+6\varepsilon & 9(1-\varepsilon) & -3(1-\varepsilon) \\ 32 & 32 & 8(1-\varepsilon) & -8(1-\varepsilon) \\ 10+6\varepsilon & 54-6\varepsilon & 3(1-\varepsilon) & -9(1-\varepsilon) \end{pmatrix} \begin{pmatrix} y_0 \\ y_1 \\ (x_1-x_0)y_0' \\ (x_1-x_0)y_1' \end{pmatrix} \quad (1)$$

[Eq. 13]

$$\begin{pmatrix} y_a' \\ y_b' \\ y_c' \end{pmatrix} = \frac{1}{16(x_1-x_0)} \begin{pmatrix} -18+2\varepsilon & 18-2\varepsilon & 3(1-\varepsilon) & -5(1-\varepsilon) \\ -24+8\varepsilon & 24-8\varepsilon & -4(1-\varepsilon) & -4(1-\varepsilon) \\ -18+2\varepsilon & 18-2\varepsilon & -5(1-\varepsilon) & 3(1-\varepsilon) \end{pmatrix} \begin{pmatrix} y_0 \\ y_1 \\ (x_1-x_0)y_0' \\ (x_1-x_0)y_1' \end{pmatrix} \quad (2)$$

Figure 3:
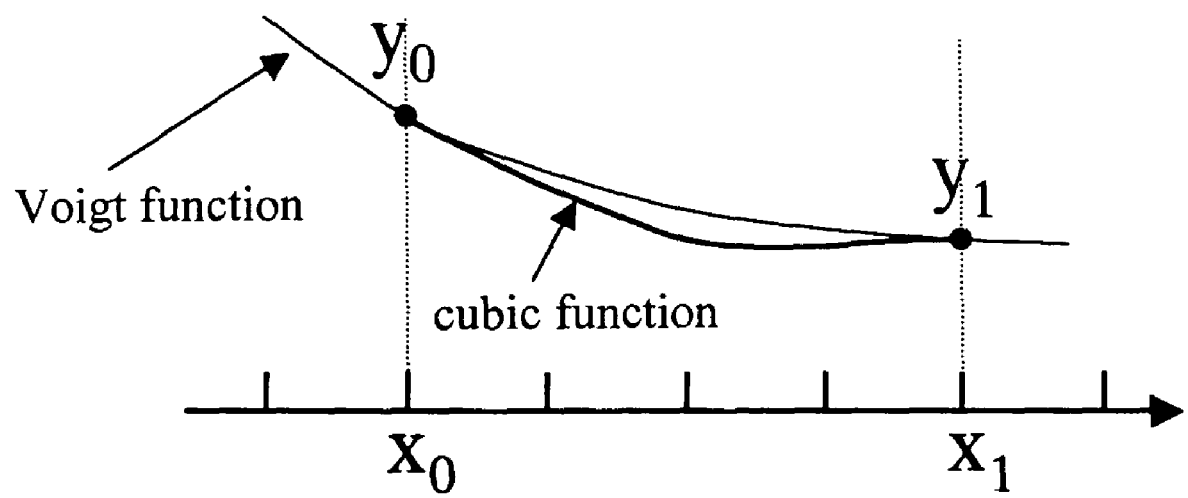
FIG. 3 is a diagram showing the error between a Voigt function and a cubic function.

Here, $\varepsilon$ is a non-negative decimal fraction. With regard to $\varepsilon$, even if the Voigt function and cubic function match at the interpolation points $x_0$, $x_1$ as shown in FIG. 3, there will be an error in the function values due to differences in the curvature of the curves in the region between the interpolation points. While adequate precision can be obtained even if E=0, the error can be further reduced by about half by changing the value of $\varepsilon$ to adjust the curvature of the cubic function. From these two equations it is possible to determine the function values $y_a$, $y_b$, $y_c$ and the derivative values $y_a'$, $y_b'$, $y_c'$ at points where the interpolation interval $(x_0, x_1)$ of the aforementioned first predetermined interval has been quartered. Here, $x_0$, $x_1$ are wave numbers in the present invention. The aforementioned adjustment of $\varepsilon$ is performed by comparing the calculation results when changing $\varepsilon$ with the calculation results for a normal line-by-line method for a small spectral range which is only a part of the spectral range to be calculated.

Additionally, the present invention proposes an interpolation in which the first predetermined interval is divided into five parts. The interpolation equations for dividing into five parts are as follows:

[Eq. 14]

$$\begin{pmatrix} y_a \\ y_b \\ y_c \\ y_d \end{pmatrix} = \quad (3)$$

$$\frac{1}{125} \begin{pmatrix} 112-12\varepsilon & 13+12\varepsilon & 16(1-\varepsilon) & -4(1-\varepsilon) \\ 81-6\varepsilon & 44+6\varepsilon & 18(1-\varepsilon) & -12(1-\varepsilon) \\ 44+6\varepsilon & 81-6\varepsilon & 12(1-\varepsilon) & -18(1-\varepsilon) \\ 13+12\varepsilon & 112-12\varepsilon & 4(1-\varepsilon) & -16(1-\varepsilon) \end{pmatrix} \begin{pmatrix} y_0 \\ y_1 \\ (x_1-x_0)y_0' \\ (x_1-x_0)y_1' \end{pmatrix}$$

[Eq. 15]

$$\begin{pmatrix} y_a' \\ y_b' \\ y_c' \\ y_d' \end{pmatrix} = \frac{1}{25(x_1-x_0)} \quad (4)$$

$$\begin{pmatrix} -24-\varepsilon & 24+\varepsilon & 8(1-\varepsilon) & -7(1-\varepsilon) \\ -36+11\varepsilon & 36-11\varepsilon & -3(1-\varepsilon) & -8(1-\varepsilon) \\ -36+11\varepsilon & 36-11\varepsilon & -8(1-\varepsilon) & -3(1-\varepsilon) \\ -24-\varepsilon & 24+\varepsilon & -7(1-\varepsilon) & 8(1-\varepsilon) \end{pmatrix} \begin{pmatrix} y_0 \\ y_1 \\ (x_1-x_0)y_0' \\ (x_1-x_0)y_1' \end{pmatrix}$$

The symbols used in the equations are the same as in the case of quartering described above. Additionally, those skilled in the art would recognize that $y_d$, $y_d'$ clearly represent a function value and a derivative value. Here, the interpolation equation described above can be used not only for the first predetermined interval, but also for other predetermined intervals, and this should also be obvious to those skilled in the art.

The interpolation points are calculated as described above. Next, as shown in FIG. 2(b), further calculations are performed by interpolation of the region around the peak in the first range. As described above, the area around the peak in the first range is called the second range 6, and divided from a skirt portion not contained in the second range 6. Then the second range is represented by a second cubic function, and the skirt portion not contained in the second range is represented by a "function representing the difference between the Voigt function and the first cubic function" 7. This second cubic function represents the difference between the new cubic function and the first cubic function. Here, this "function representing the difference between the Voigt function and the first cubic function" shall henceforth be referred to simply as the "difference function". As described above, the second cubic function and the "difference function" 7 are again joined under the condition that at the points of connection, the function values and derivative values are matched.

After connecting the functions in this way, the function value and derivative value are calculated in the second predetermined interval for the second range. This second predetermined interval is smaller than the first predetermined interval and is calculated by the equation given below.

For the sub-function with the (k−kmin+1)-th smallest width, the predetermined interval is $j^k dv$. Here, j is a single-digit natural number, dv is the increase in wave number and k is such that $kmin \leq k < kmax$.

Additionally, these calculations are performed for all absorption lines. Furthermore, interpolation is performed between the calculated points. The equations (1) and (2) or (3) and (4) are used for the interpolation.

Here, the above method for calculating a "difference function" for a skirt portion not contained in the second range and a cubic function for the second range that connects smoothly therewith for a plurality of absorption lines has been explained, but it is also possible to use a method of calculating the Voigt function of the skirt portion not contained in the second range and a cubic function connecting smoothly therewith for a plurality of absorption lines, then subtracting the first cubic function from the entire first range for a plurality of absorption lines.

With regard to this second range, the above calculations may be repeated until a predetermined interval is reached. That is, the second range may be further divided into a peak area and a skirt portion which are respectively calculated by a cubic function and difference function, then connected, and the calculation performed with k in the equation for calculating the second predetermined interval incremented by 1. This calculation is performed for all absorption lines, and these are added to the results calculated in FIG. 2(b). The steps described above are repeated until the predetermined interval is reached.

Further, a calculation is performed after replacing the peak area with a cubic function and making the skirt portion a "difference function", over a third predetermined interval smaller than the second interval. This third predetermined interval is represented by the equation given below. The third predetermined interval is $j^{kmin}dv$. Here, j is a single-digit natural number, dv is the increment of the wave number, and kmin is the maximum non-negative decimal fraction satisfying the relationship $j^{kmin}pdv \leq \alpha$ (if non-existent, it is set to 0). However, α has a value of about γ/4 (γ being an estimate of the full width at half max of the absorption line), and p is a natural number (p=1, 2, 3) controlling the calculation precision.

By following the above steps, it is possible to calculate a Voigt function precisely and at high speed. Here, it is known that there is a slight difference from the Voigt function of carbon dioxide and the like, and a method for correcting for this difference is known. The method of the present invention can also be applied to such corrections. These corrections shall be explained next.

General profile correction shall be explained first.

The Voigt function is represented by K(x, y). When the difference from the Voigt profile is represented by the shape of $K(x, y) + f(x)$, the high-speed technique can be applied by setting:

$$\tilde{K}(x,y) \quad [\text{Eq. 16}]$$

as the function to be substituted, and replacing it with:

$$\tilde{K}(x, y) = AK(x, y) + Bf(x) \quad [\text{Eq. 17}]$$

$$\frac{\partial \tilde{K}(x, y)}{\partial x} = A\frac{\partial K(x, y)}{\partial x} + B\frac{\partial f(x)}{\partial x} \quad [\text{Eq. 18}]$$

Similarly, if the difference from the Voigt profile is represented by the shape of $K(x, y)f(x)$, then the high-speed technique can be performed by replacing it with $$\tilde{K}(x, y) = K(x, y)f(x) \quad [\text{Eq. 19}]$$

$$\frac{\partial \tilde{K}(x, y)}{\partial x} = \frac{\partial K(x, y)}{\partial x}f(x) + K(x, y)\frac{\partial f(x)}{\partial x} \quad [\text{Eq. 20}]$$

Explaining the above correction method with a specific example, in a sub-Lorentzian correction:

$$K(x, y) \quad [\text{Eq. 21}]$$

$$\frac{\partial K(x, y)}{\partial x} \quad [\text{Eq. 22}]$$

will respectively become:

$$\tilde{K}(x, y) = K(x, y)A\exp(-B|x|) \quad [\text{Eq. 23}]$$

$$\frac{\partial \tilde{K}(x, y)}{\partial x} = \quad [\text{Eq. 24}]$$

$$\frac{\partial K(x, y)}{\partial x}A\exp(-B|x|) + K(x, y)[-sgn(x)AB\exp(-B|x|)]$$

Here, A and B are correction coefficients. Additionally, those skilled in the art will recognize that sgn(x) is the sign function.

For line-mixing correction, the following relationships arise:

$$\frac{\partial K(x, y)}{\partial x} = 2[yL(x, y) - xK(x, y)] \quad [\text{Eq. 25}]$$

$$\frac{\partial L(x, y)}{\partial x} = 2\left[xL(x, y) + yK(x, y) - \frac{1}{\sqrt{\pi}}\right] \quad [\text{Eq. 26}]$$

Therefore, $$K(x, y) \quad [\text{Eq. 27}]$$

$$\frac{\partial K(x, y)}{\partial x} \quad [\text{Eq. 28}]$$

will respectively be $$\tilde{K}(x, y) = AK(x, y) + BL(x, y) \quad [\text{Eq. 29}]$$

$$\frac{\partial \tilde{K}(x, y)}{\partial x} = -2\left[(Ax + By)K(x, y) - (Ay - Bx)L(x, y) - \frac{B}{\sqrt{\pi}}\right] \quad [\text{Eq. 30}]$$

Here, L(x, y) is the imaginary component of the function w(z), where complex number z=x+iy, defined by the following equation. The real part is the Voigt function.

$$w(z) = \quad [\text{Eq. 31}]$$

$$\frac{i}{\pi}\int_{-\infty}^{\infty}\frac{\exp(-t^2)}{z-t}dt = \exp(-z^2)\text{erfc}(-iz) = K(x, y) + iL(x, y)$$

erfc(z) is a complex complementary error function.

According to the calculation methods of the present invention described above, it is possible to perform line-by-line calculations using Voigt functions with good precision and at high speed. By further loading these methods as computer programs, it is possible to result in specific devices. Such a program may, for example, be a stand-alone type program operating on a personal computer. It may also be provided in the form of a plug-in for other software.

The invention claimed is:

1. A method for increasing the speed of line-by-line calculations of multiple overlapping absorption lines, said method comprising:

(1) a step of dividing a domain of a Voigt function representing the shape of an absorption line into a first range around the peak of the Voigt function and a skirt portion not contained in the first range, replacing the first range with a cubic function whose function values and derivative values match with those of said Voigt function at the connection points with said Voigt function, and calculating the values and derivative values of said cubic function and the Voigt function in the skirt portion for each of first predetermined intervals;

(2) a step of adding together the results of step (1) for a plurality of absorption lines;

(3) a step of interpolating the results of step (2) to calculate the function values and derivative values in second predetermined intervals smaller than said first predetermined intervals;

(4) a step of dividing said first range into a second range near the peak of said cubic function and a skirt portion not contained in the second range, replacing said second range of a "function representing the difference between the Voigt function and said cubic function" with a second cubic function whose function values and derivative values match with those of said "function representing the difference between the Voigt function and said cubic function" at the connection points with said "function representing the difference between the Voigt function and said cubic function", and calculating the values and derivative values of said second cubic function replacing said second range and the "function representing the difference between the Voigt function and said cubic function" in the skirt portion for said second predetermined intervals;

(5) a step of adding the results of step (4) to the results of step (3) for a plurality of absorption lines;

(6) a step of interpolating the results of step (5) to calculate the function values and derivative values for intervals smaller than said second predetermined intervals; and (7) a step of adding the values and derivative values of the "function representing the difference between the ""function representing the difference between the Voigt function and said cubic function""and said second cubic function" to the results of step (6) for a plurality of absorption lines in said second range.

2. A method in accordance with claim 1, wherein (8) the step of calculating function values and derivative values by interpolation is repeated while narrowing the interval until it becomes an interval of a minimum unit.

3. A method in accordance with claim 1, wherein said steps (4) through (6) are repeated one or more times until the "intervals smaller than said second predetermined intervals" in step (6) reach third predetermined intervals.

4. A method in accordance with claim 1, wherein said predetermined interval is determined by using the following equation:

said first predetermined intervals are $j^{kmax}dv$; here, j is a single-digit natural number, dv is the increment in wave number, and kmax is the largest natural number satisfying the relationship $j^{kmax+2}pdv \leq Vmax$, where Vmax represents the maximum calculation range from the center of the absorption line, and p is a natural number for controlling the calculation precision.

5. A method in accordance with claim 3, wherein said predetermined interval is determined using the following equation:

the third predetermined intervals are $j^{kmin}dv$; here, j is a single-digit natural number, dv is the increment of the wave number, and kmin is the maximum non-negative decimal number satisfying the relationship $j^{kmin}pdv \leq \alpha$ ($\alpha$ being approximately $\gamma/4$) where $\gamma$ is an approximate value of the full-width at half-maximum of the absorption line, and p is a natural number for controlling the calculation precision.

6. A method in accordance with claim 1, wherein said second predetermined interval is determined by using the following equation:

for the sub-function with the (k−kmin+1)—th smallest width, the predetermined interval is $j^k dv$; here j is a single-digit natural number, dv is the increase in wave number and k is such that kmin≦k<kmax; kmax is a natural number satisfying the relationship $j^{kmax+2}pdv \leq Vmax$, where Vmax represents the maximum calculation range from the center of the absorption line, and p is a natural number for controlling the calculation precision; kmin is the maximum non-negative decimal number satisfying the relationship $j^{kmin}pdv \leq \alpha$ ($\alpha$ being approximately $\gamma/4$), where $\gamma$ is an approximate value of the full-width at half-maximum of the absorption line, and p is a natural number for controlling the calculation precision.

7. A method in accordance with any one of claims 1-3, wherein said interpolation is calculated by quartering the interpolation interval, with the function values represented by $y_a, y_b, y_c$ and the derivative values represented by $y_a', y_b', y_c'$ at the points where the interpolation interval $(x_0, x_1)$ is divided, using the function values $y_0, y_1$ and function derivative values $y_0', y_1'$ at $x_0, x_1$, with the below-given Equation (1) as a function value interpolation equation, Equation (2) as a function derivative value interpolation equation and $\epsilon$ as a non-negative decimal fraction:

$$\begin{pmatrix} y_a \\ y_b \\ y_c \end{pmatrix} = \frac{1}{64} \begin{pmatrix} 54-6\varepsilon & 10+6\varepsilon & 9(1-\varepsilon) & -3(1-\varepsilon) \\ 32 & 32 & 8(1-\varepsilon) & -8(1-\varepsilon) \\ 10+6\varepsilon & 54-6\varepsilon & 3(1-\varepsilon) & -9(1-\varepsilon) \end{pmatrix} \begin{pmatrix} y_0 \\ y_1 \\ (x_1-x_0)y_0' \\ (x_1-x_0)y_1' \end{pmatrix} \quad (1)$$

$$\begin{pmatrix} y_a' \\ y_b' \\ y_c' \end{pmatrix} = \frac{1}{16(x_1-x_0)} \begin{pmatrix} -18+2\varepsilon & 18-2\varepsilon & 3(1-\varepsilon) & -5(1-\varepsilon) \\ -24+8\varepsilon & 24-8\varepsilon & -4(1-\varepsilon) & -4(1-\varepsilon) \\ -18+2\varepsilon & 18-2\varepsilon & -5(1-\varepsilon) & 3(1-\varepsilon) \end{pmatrix} \begin{pmatrix} y_0 \\ y_1 \\ (x_1-x_0)y_0' \\ (x_1-x_0)y_1' \end{pmatrix}. \quad (2)$$

8. A method in accordance with any one of claims 1-3, wherein said interpolation is calculated by dividing the interpolation interval into five parts, with the function values represented by $y_a, y_b, y_c, y_d$ and the derivative values represented by $y_a', y_b', y_c', y_d'$ at the points where the interpolation interval $(x_0, x_1)$ is divided, using the function values $y_0, y_1$ and function derivative values $y_0', y_1'$ at $x_0, x_1$, with the below-given Equation (3) as a function value interpolation equation, Equation (4) as a function derivative value interpolation equation and $\epsilon$ as a non-negative decimal fraction:

$$\begin{pmatrix} y_a \\ y_b \\ y_c \\ y_d \end{pmatrix} = \qquad (3)$$

$$\frac{1}{125} \begin{pmatrix} 112-12\varepsilon & 13+12\varepsilon & 16(1-\varepsilon) & -4(1-\varepsilon) \\ 81-6\varepsilon & 44+6\varepsilon & 18(1-\varepsilon) & -12(1-\varepsilon) \\ 44+6\varepsilon & 81-6\varepsilon & 12(1-\varepsilon) & -18(1-\varepsilon) \\ 13+12\varepsilon & 112-12\varepsilon & 4(1-\varepsilon) & -16(1-\varepsilon) \end{pmatrix} \begin{pmatrix} y_0 \\ y_1 \\ (x_1-x_0)y'_0 \\ (x_1-x_0)y'_1 \end{pmatrix}$$

$$\begin{pmatrix} y'_a \\ y'_b \\ y'_c \\ y'_d \end{pmatrix} = \frac{1}{25(x_1-x_0)} \qquad (4)$$

$$\begin{pmatrix} -24-\varepsilon & 24+\varepsilon & 8(1-\varepsilon) & -7(1-\varepsilon) \\ -36+11\varepsilon & 36-11\varepsilon & -3(1-\varepsilon) & -8(1-\varepsilon) \\ -36+11\varepsilon & 36-11\varepsilon & -8(1-\varepsilon) & -3(1-\varepsilon) \\ -24-\varepsilon & 24+\varepsilon & -7(1-\varepsilon) & 8(1-\varepsilon) \end{pmatrix} \begin{pmatrix} y_0 \\ y_1 \\ (x_1-x_0)y'_0 \\ (x_1-x_0)y'_1 \end{pmatrix}.$$

9. A method in accordance with any one of claims 1-8, for increasing the speed of line-by-line calculations, when assuming the Voigt function to be K(x, y) and the shape of the absorption line displaced from the Voigt profile of the absorption line to be K(x, y)+ƒ(x), by replacing $K(x, y)$ with:

$\tilde{K}(x, y) = AK(x, y) + Bf(x)$ and $\dfrac{\partial K(x, y)}{\partial x}$ with $\dfrac{\partial \tilde{K}(x, y)}{\partial x} = A \dfrac{\partial K(x, y)}{\partial x} + B \dfrac{\partial f(x)}{\partial x}.$

10. A method in accordance with any one of claims 1-8, for increasing the speed of line-by-line calculations, when assuming the Voigt function to be K(x, y) and the shape of the absorption line displaced from the Voigt profile to be K(x, y)ƒ(x), by replacing $K(x, y)$ with:

$\tilde{K}(x, y) = K(x, y)f(x)$ and $\dfrac{\partial K(x, y)}{\partial x}$ with $\dfrac{\partial \tilde{K}(x, y)}{\partial x} = \dfrac{\partial K(x, y)}{\partial x} f(x) + K(x, y) \dfrac{\partial f(x)}{\partial x}.$

11. A method in claim 10, for increasing the speed of line-by-line calculations, by using, in a sub-Lorentzian correction, $\tilde{K}(x, y) = K(x, y) A \exp(-B|x|)$ and $\dfrac{\partial \tilde{K}(x, y)}{\partial x} = \dfrac{\partial K(x, y)}{\partial x} A \exp(-B|x|) + K(x, y)[-sgn(x)AB\exp(-B|x|)].$

12. A method in accordance with claim 9, for increasing the speed of line-by-line calculations, by replacing, in a line-mixing correction, $K(x, y)$ with:

$\tilde{K}(x, y) = AK(x, y) + BL(x, y)$ and $\dfrac{\partial K(x, y)}{\partial x}$ with $\dfrac{\partial \tilde{K}(x, y)}{\partial x} = -2\left[(Ax+By)K(x, y) - (Ay-Bx)L(x, y) - \dfrac{B}{\sqrt{\pi}}\right];$ here, L(x, y) is the imaginary component of the function w(z) (the real part is the Voigt function), where complex number z=x+iy, defined by the following equation:

$$w(z) = \dfrac{i}{\pi} \int_{-\infty}^{\infty} \dfrac{\exp(-t^2)}{z-t} dt = \exp(-z^2)\mathrm{erfc}(-iz) = K(x, y) + iL(x, y)$$

(erfc(z) is a complex complementary error function).

13. A non-transitory computer-readable medium containing a program for increasing the speed of line-by-line calculations of multiple overlapping absorption lines, said program when executed by a computer performs:

(1) a step of dividing a domain of a Voigt function representing the shape of an absorption line into a first range around the peak of the Voigt function and a skirt portion not contained in the first range, replacing the first range with a cubic function whose function values and derivative values match with those of said Voigt function at the connection points with said Voigt function, and calculating the values and derivative values of said cubic function and the Voigt function in the skirt portion for each of first predetermined intervals;

(2) a step of adding together the results of step (1) for a plurality of absorption lines;

(3) a step of interpolating the results of step (2) to calculate the function values and derivative values in second predetermined intervals smaller than said first predetermined intervals;

(4) a step of dividing said first range into a second range near the peak of said cubic function and a skirt portion not contained in the second range, replacing said second range of a "function representing the difference between the Voigt function and said cubic function" with a second cubic function whose function values and derivative values match with those of said "function representing the difference between the Voigt function and said cubic function" at the connection points with said "function representing the difference between the Voigt function and said cubic function", and calculating the values and derivative values of said second cubic function replacing said second range and the "function representing the difference between the Voigt function and said cubic function" in the skirt portion for said second predetermined intervals;
(5) a step of adding the results of step (4) to the results of step (3) for a plurality of absorption lines;
(6) a step of interpolating the results of step (5) to calculate the function values and derivative values for intervals smaller than said second predetermined intervals; and
(7) a step of adding the values and derivative values of the "function representing the difference between the""function representing the difference between the Voigt function and said cubic function""and said second cubic function" to the results of step (6) for a plurality of absorption lines in said second range.

14. A non-transitory computer-readable medium in accordance with claim 13, wherein the step of calculating function values and derivative values by interpolation is repeated while narrowing the interval until it becomes an interval of a minimum unit.

15. A non-transitory computer-readable medium in accordance with claim 13, wherein said steps (4) through (6) are repeated one or more times until the "intervals smaller than said second predetermined intervals" in step (6) reach third predetermined intervals.

* * * * *